United States Patent [19]

Onishi et al.

[11] Patent Number: 4,886,916
[45] Date of Patent: Dec. 12, 1989

[54] PROCESS FOR PREPARING SULFONE COMPOUNDS

[75] Inventors: Takashi Onishi; Shigeaki Suzuki; Toshiki Mori; Hiroshi Fujii, all of Kurashiki; Yoshiji Fujita, Yokohama, all of Japan

[73] Assignee: Kuraray Company, Ltd., Okayama, Japan

[21] Appl. No.: 168,408

[22] Filed: Mar. 15, 1988

[30] Foreign Application Priority Data

Mar. 17, 1987 [JP] Japan .................................. 62-63414
Mar. 17, 1987 [JP] Japan .................................. 62-63415

[51] Int. Cl.$^4$ .................. C07C 147/02; C07C 147/04
[52] U.S. Cl. ........................................ 568/34; 568/28
[58] Field of Search ................ 568/28, 34; 570/231, 570/217

[56] References Cited

U.S. PATENT DOCUMENTS 2,794,826  6/1957  Bell et al. ........................... 570/231
2,862,015 11/1958  Kundiger et al. .................. 570/217
3,781,313 12/1973  Julia .................................... 568/34
4,704,485 11/1987  Mitchell et al. ................... 570/231

FOREIGN PATENT DOCUMENTS 463912  7/1973  Australia .
53-20030 6/1978  Japan .

OTHER PUBLICATIONS

P. Grieco et al., J. Org. Chem., vol. 39, No. 14, 2135, (1974).
K. Inomata et al., Chemistry Letters, 1357–1360, (1981).
Derwent Abstract of Japanese Patent Laid—Open No. 56-86149.
Derwent Abstract of Japanese Patent Laid—Open No. 58-52267.
Derwent and Japio Abstracts of Japanese Patent Publication No. 57-48549, Torii et al.
J. Org. Chem., (1986), vol. 51, pp. 3834–3838, "Stereocontrolled Synthesis of Vitamin A Through a Double Elimination Reaction", Junzo Otera, et al.
J. Org. Chem., (1985), vol. 50, pp. 1327–1329, "Synthesis of Sulfones by Phase—Transfer Alkylation of Arenesulfinate Salts", Jack Crandall, et al.
J. Org. Chem., (1974), pp. 2135–2136, "A General 1,5 Diene Synthesis. Application to the Synthesis of Squalene", Paul A. Grieco, et al.
Chemistry Letters, (1981), pp. 1357–1360, "Regio— and Stereocontrolled Synthesis of Allylic p–Tolyl Sulfones Catalyzed by Palladium (O) Complex", K. Inomata, et al.
Synthesis, Sep. 1979, pp. 733–734, Georg Thieme Publishers, Wildeman et al, Convenient Alternative Synthesis of Sulfones . . . .

Primary Examiner—Mary E. Ceperley
Attorney, Agent, or Firm—Oblon, Spivak, McClelland, Maier & Neustadt

[57] ABSTRACT

A process for preparing an allylic sulfone of the following general formula (I),

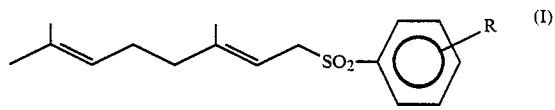

wherein, R is a hydrogen atom or a lower alkyl group, and containing both cis and trans isomers, by a reaction of a compound selected from the group consisting of geranyl chloride, neryl chloride, and linalyl chloride with a phenyl sulfinate of the following general formula (III),

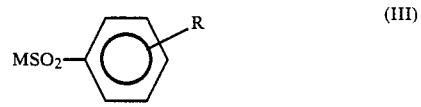

wherein, R is a hydrogen atom, or a lower alkyl group, and M is a sodium atom or potassium atom, in the presence of (i) tetralkylammonium iodide in an anhydrous condition or (ii) a zinc halide and an iodide.

12 Claims, No Drawings

PROCESS FOR PREPARING SULFONE COMPOUNDS

BACKGROUND OF THE INVENTION

1. Field of the Invention

This invention relates to a process for preparing allylic sulfones of the general formula (I),

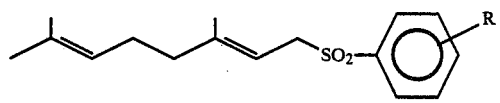

wherein R is a hydrogen atom or a lower alkyl group, and containing both cis and trans isomers, or cyclogeranyl sulfone of general formula (II),

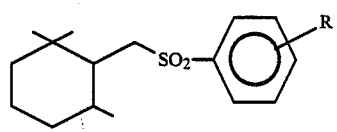

wherein R is a hydrogen atom or a lower alkyl group, and a double bond exists at either one of the positions of the dotted bonds.

The allylic sulfone of general formula (I) and cyclogeranyl sulfone of general formula (II) are useful as intermediates for preparing vitamin A or vitamin A acetate used as a drug or a feed additive. (See Japanese Patent Publication No. 57-48549, and Otera et al. J. Org. Chem. 51, 3834 (1986)).

DESCRIPTION OF THE RELATED ART

Processes for preparing allylic sulfones from phenyl sulfinates classified according to functional group are shown as follows (A)

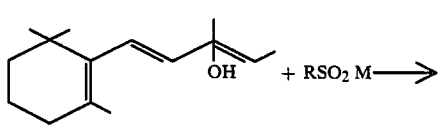

(See, Japanese Patent Publication No. 53-20030

(B)

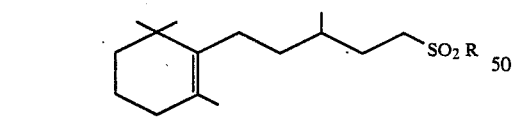

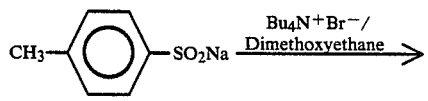

(See, J. Wildeman et al., Synthesis, 733 (1979))

(b)

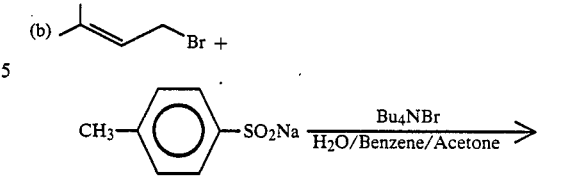

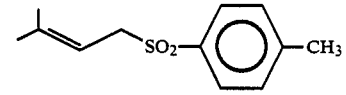

(See, J. Org. Chem., 50 1327 (1985))

(c)

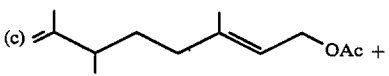

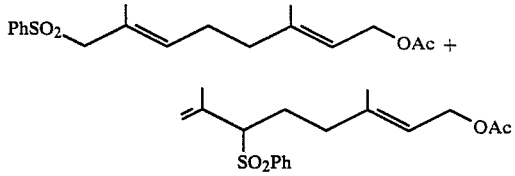

(See, Japanese Patent Laid-Open No. 58-52267)

(d)

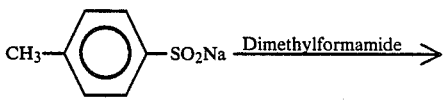

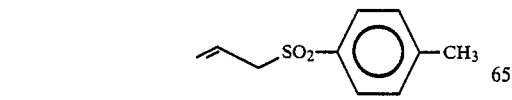

(See, J. Org. Chem., 39, 2135 (1974))

(C)

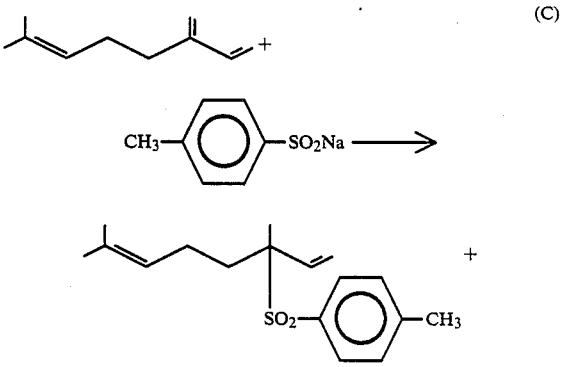

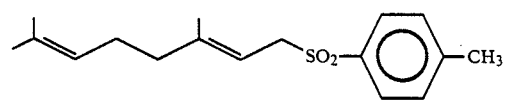

(See, Japanese Patent Laid-Open No. 56-86149)

3

-continued

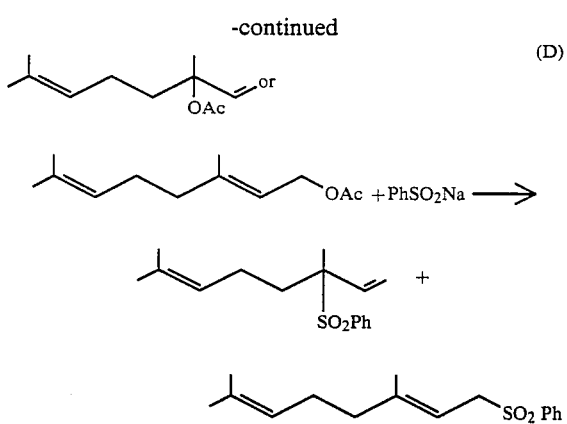

(See, Inomata et al., Chem. Lett., 1357 (1981))

Among these processes preparing for allylic sulfones, the process (B) is frequently applied from the standpoint of operability. Particularly the corresponding primary allylic sulfone is well known as easily prepared according to the reaction of a primary allylic halide with phenyl sulfinate. According to these literature references, a primary allylic halide is well known as easily transformed to the corresponding primary allylic sulfone, there is no description of, and no other literature references describing the reaction of a tertiary allylic halide with phenyl sulfinates, and the synthesis of primary allylic sulfone by this reaction. According to the inventor's experience, the yield of allylic sulfone based on allylic halides in the ordinary reaction of a mixture of primary and tertiary allylic halide with phenyl sulfinates is not satisfactory because of the low reactivity of tertiary allylic halides with phenyl sulfinates. Particularly the process (B)-d preparing geranyl p-tolyl sulfone from geranyl bromide as the starting material, which must be synthesized from expensive geraniol and phosphorus tribromide, is not proper for a commercial production at a reasonable cost.

A process for preparing cyclogeranyl sulfone by the cyclization of geranyl phenyl sulfone under acidic conditions is known.

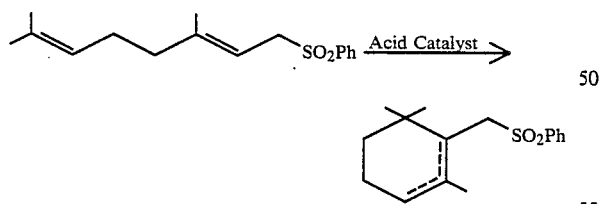

This process for preparing cyclogeranyl phenyl sulfone could not be applied on a commercial scale until recently because of the lack of a process for preparing cyclogeranyl phenyl sulfone on a commercial scale.

An object of the invention is to provide a process for preparing an allylic sulfone of general formula (I) and a cyclogeranyl phenyl sulfone of general formula (II) on a commercial scale production in high yield with a low price and easily obtainable raw material.

Other objects, features and advantages of the invention will become apparent from the following description.

4

SUMMARY OF THE INVENTION

According to the invention, there is provided a process for preparing allylic sulfones of general formula (I) by the reaction of a compound selected from the group consisting of geranyl chloride, neryl chloride, and linalyl chloride with a phenyl sulfinate of general formula (III),

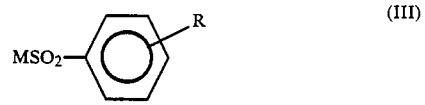

wherein R is a hydrogen atom or a lower alkyl group, and M is a sodium or potassium atom, in the presence of (i) tetralkylammonium iodide under anhydrous conditions, or (II) a zinc halide and an iodide.

DESCRIPTION OF THE PREFERRED EMBODIMENTS

In the above mentioned general formulas (I), (II), and (III), R is a hydrogen atom, or a lower alkyl group, such as methyl, ethyl, n-propyl, i-propyl, n-butyl, i-butyl, t-butyl group and the like, which may be substituted at any position of ortho-(o-), meta-(m-), and para-(p-) positions relative to the sulfinic group. Preferably, R is a hydrogen atom, or a methyl group. M is a sodium or potassium atom.

According to the invention, the amount of phenyl sulfinate of general formula (III) used is equimolar or more, more particularly in the range of from 1 to 2 times in moles to the amount of the compound selected from the group consisting of geranyl chloride, neryl chloride, and linalyl chloride.

According to the invention, the reaction of a compound selected from the group consisting of geranyl chloride, neryl chloride, and the linalyl chloride, with phenyl sulfinate of general formula (III), is conducted in the presence of (i) tetralkylammonium iodide in an anhydrous system, or (II) a zinc halide and an iodide.

The description on the reaction using (i) tetralkylammonium iodide is as follows.

The sum of carbon number of the four alkyl groups in tetralkylammonium iodide is preferably in the range of from 8 to 32. Examples are tetra-n-butylammonium iodide, tetra-n-pentylammonium iodide, and stearyltrimethylammonium iodide.

The effect of the presence of tetralkylammonium iodide is to obtain the primary allylic sulfone in high yield suppressing the formation of tertiary allylic sulfone of the general formula (IV),

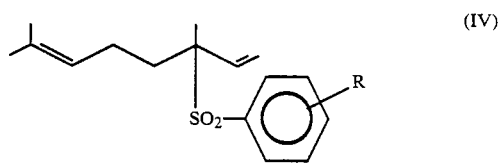

where, R is a hydrogen atom or a lower alkyl group.

As is obvious in the following examples, the process of the invention using tetralkylammonium iodide as the catalyst is superior when compared to the process using tetralkylammonium bromide as the catalyst from the standpoint of yield.

Tetralkylammonium iodide is usually used in an amount of from 0.1 to 30 mole percent, preferably from 0.2 to 10 mole percent per mole of the compound selected from the group of compounds consisting of geranyl chloride, neryl chloride, and linalyl chloride.

The reaction can be conducted in a solvent. Examples of such a solvent used for the reaction include aliphatic hydrocarbons, such as hexane, heptane, octane and the like, and aromatic hydrocarbons, such as benzene, toluene, xylene and the like. Preferably an aromatic hydrocarbon is used. The advantages of using such a solvent of hydrocarbon are as follows:

1. The solvent insoluble in water can be used as an extraction solvent for the reaction mixture at the work-up stage, so that the addition of a new extraction solvent is not needed.

2. The presence of water decreases the yield of allylic sulfone (See Comparative Example 2). The water associated with the phenyl sulfinate can be removed from the reaction zone by the azeotropic dehydration method with a hydrocarbon solvent, such as toluene and the like.

The reaction temperature is favorably in the range of from 0° C. to 150° C., more preferably from 50° C. to 120° C. The reaction time, depending on the reaction conditions, is within 3 hours, when the reaction temperature is maintained at about 100° C.

The following is a description of the reaction using (ii) a zinc halide and an iodide.

By the reaction of a phenyl sulfinate of general formula (III) with a compound selected from the group consisting of geranyl chloride, neryl chloride, and linalyl chloride, in the presence of a zinc halide and an iodide, a primary allylic sulfone of general formula (I) can be obtained in high yield because linalyl chloride can be used in the reaction with phenyl sulfinate as in the case of geranyl chloride or neryl chloride.

Zinc halides are, for example, zinc chloride, zinc bromide, and zinc iodide, preferably zinc chloride. The amount of zinc halide is preferably in the range of from 1 mole percent to 1 mole equivalent per mole of the compound selected from the group consisting of geranyl chloride, neryl chloride and linalyl chloride. Iodides are alkali salts of hydroiodic acid, such as, sodium iodide, potassium iodide and the like. The amount of the iodide is in the range of from 1 mole percent to 1 mole equivalent per mole of the compound selected from the group consisting of geranyl chloride, neryl chloride and linalyl chloride. The use of iodide in amounts more than 1 mole equivalent does not inhibit the reaction, but also does not improve the yield.

The reaction is generally conducted in a polar solvent, such as dimethyl formamide, diethyl formamide, N-methyl-pyrrolidone and the like, which are stable in the reaction zone and can dissolve the phenyl sulfinate, zinc halides, and iodide The amount of the solvent is in the range of from 0.5 to 50 times by volume of the compound selected from the group consisting of geranyl chloride, neryl chloride, and linalyl chloride.

The reaction is generally conducted by maintaining the inner temperature in the range of from 0° C. to 150° C., preferably from 30° C. to 100° C. under stirring. The reaction is preferably conducted under an inert gas atmosphere, such as nitrogen, argon, helium or the like. The reaction time, depending on the reaction conditions, is within 10 hours when the inner temperature is maintained in the range of from 60° C. to 70° C.

Geranyl chloride, neryl chloride, and linalyl chloride used as a raw material can be prepared by the reaction of myrcene with hydrogen chloride, or the reaction of linalool with thionyl chloride. The reaction of myrcene with hydrogen chloride, or linalool with thionyl chloride usually provides a mixture of geranyl chloride, neryl chloride, and linalyl chloride. The thus obtained mixture of geranyl chloride, neryl chloride and linalyl chloride can be used in the reaction of phenyl sulfinates of general formula (III).

The reaction of myrcene with hydrogen chloride is generally conducted in the presence of a copper catalyst. Examples of preferred copper catalysts are cuprous or cupric compounds of chloride, bromide, carbonate, formate, acetate, sulfate, oxide and the like, preferably cuprous chloride.

The amount of catalyst is in the range of from 0.01 to 10 percent by weight per weight of dried myrcene. The amount of hydrogen chloride used for the reaction is favorably in the rang of from 0.8 to 1.2 moles per mole of myrcene. When more than 1.2 moles of hydrogen chloride is used, the yield of linalyl chloride, neryl chloride, and geranyl chloride is decreased by the addition reactions of the excess hydrogen chloride. The reaction temperature is favorably in the range of from −20° C. to 50° C., more preferably from −5° C. to 20° C. The presence of organic sulfide increases the content of geranyl chloride and neryl chloride in the reaction mixture at the end of hydrogen chloride gas bubbling.

The organic sulfides used for this purpose are the sulfides having as an organic group, aliphatic or cyclic alkyl groups of from one to about 20 carbon atoms, such as methyl, ethyl, n-propyl, n-butyl, i-butyl, cyclohexyl, n-hexyl, n-octyl, myristyl, stearyl and the like, or aryl groups, such as phenyl, p-tolyl, naphthyl and the like, or aralkyl groups, such as benzyl, β-phenylethyl and the like. Examples of the sulfides are n-hexyl sulfide, n-octyl sulfide, t-butyl n-octyl sulfide, phenyl sulfide, cyclohexyl sulfide, benzyl sulfide and the like. The amount of the organic sulfide is preferably in the range of from about 0.1 to 5 percent, more preferably from about 0.5 to 2 percent by weight to the weight of myrcene.

Organic hydrocarbon solvents, such as hexane, heptane and the like, or halogenated hydrocarbons, such as dichloromethane, 1,2-dichloroethane and the like, are used when necessary in the reaction of myrcene with hydrogen chloride. Although the amount of organic solvent is not critical, the use of about 100 g or less of organic solvent per gram of myrcene is preferable. This hydrochlorination reaction is carried out by bubbling hydrogen chloride gas into the mixture of myrcene, copper catalyst, and an organic sulfide when necessary, with or without solvent.

The reaction of linalool with thionyl chloride is generally conducted in a hydrocarbon solvent such as hexane, benzene, toluene or the like, or ethers such as diethyl ether, isopropyl ether or the like. The use of an amine, such as pyridine, triethylamine or the like, reacting with hydrogen chloride generated by the reaction, is preferable. The amount of amine is at least 0.5 moles per mole of linalool, preferably at least equimolar to the amount of linalool. The reaction temperature is in the range of from 0° C. to 70° C., preferably from 20° C. to 40° C.

The allylic sulfone of general formula (I) obtained by the above mentioned process is cyclized to cyclogeranyl phenyl sulfone of general formula (II) in the presence of an acid catalyst.

The acids which can be effectively used in the cyclization reaction are, for example, sulfuric acid, the mixture of sulfuric acid with water, and sulfuric acid with a lower aliphatic carboxylic acid, such as formic acid, acetic acid and the like. The amount of acid is in the range of from about 0.1 to 20 moles preferably from 0.3 to 5 moles to the amount of allylic sulfone. The reaction temperature, depending on the kind and amount of acid, is usually in the range of from −10° C. to 150° C. for a period of from 1 minute to 10 hours. Although it is not essential to use a solvent for the reaction, solvents may be used for the purpose of improving the stirring state with the decrease of system viscosity, and facilitating the control of reaction temperature by adding a solvent of low boiling point.

The solvents for this purpose, which are stable in the reaction zone and inert to the reaction, are aliphatic hydrocarbons, such as butane, pentane, hexane, heptane and the like, halogenated hydrocarbons, such as methyl chloride, propyl chloride, ethylene dichloride and the like, aliphatic ethers, such as methyl ether, ethyl ether, propyl ether and the like, aliphatic ketones, such as acetone, methyl ethyl ketone, methyl propyl ketone, diisopropyl ketone and the like, and esters of aliphatic carboxylic acid, such as methyl acetate, ethyl acetate and the like. The amount of solvent is preferably in the range of from 0.1 to 100 times by volume to the amount of acid.

The cyclogeranyl phenyl sulfone of general formula (II) obtained by a process of this invention is a mixture of α-cyclogeranyl phenyl sulfone of general formula (II-1) and β-cyclogeranyl phenyl sulfone of general formula (II-2).

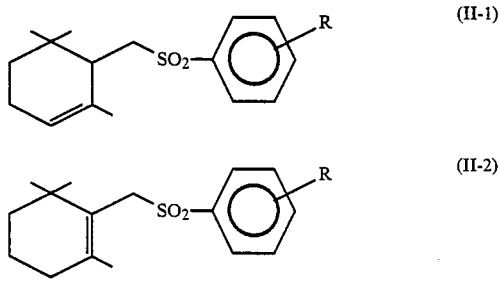

wherein R is a hydrogen atom or a lower alkyl group.

The ratio of the compound of general formula (II1) and (II-2), (II-1)/(II-2) in the above mentioned mixture is 10-40/90-60. β-cyclogeranyl phenyl sulfone of general formula (II-2), intermediates for the preparation of vitamin A and vitamin A acetate, can be separated by crystallization from a mixture by cyclogeranyl phenyl sulfone containing predominantly β-cyclogeranyl phenyl sulfone. The crystallization solvents, singly or mixed, are aliphatic hydrocarbons, such as benzene, toluene, xylene and the like, aliphatic ethers such as ethyl ether, propyl ether and the like, aliphatic alcohols such as methanol, ethanol, propanol and the like, and esters of carboxylic acids such as methyl acetate, ethyl acetate and the like. The temperature of crystallization, depending on the solvent, is usually in the range of from reflux temperature to −50° C. The amount of solvent is in the range of from 0.1 to 200 times by volume to the amount of cyclogeranyl phenyl sulfone. Although it is not essential to use a solvent for the separation of the compound of general formula (II-1) and (II-2) by crystallization, generally β-cyclogeranyl phenyl sulfone with high purity can be separated by using a solvent. The separation by crystallization can also be conducted under high pressure.

The mixture of α-cyclogeranyl phenyl sulfone and β-cyclogeranyl phenyl sulfone, predominant of α-cyclogeranyl phenyl sulfone, is recovered by the removal of solvent, when a solvent is used, by distillation under normal or reduced pressure from the mother liquor from which β-cyclogeranyl phenyl sulfone is obtained by crystallization. The reaction of the thus obtained mixture, singly or mixed with allylic sulfone of general formula (I), with an acid provides a mixture of α-cyclogeranyl phenyl sulfone and β-cyclogeranyl phenyl sulfone, predominantly of β-cyclogeranyl phenyl sulfone, from which β-cyclogeranyl phenyl sulfone is obtained by crystallization under the same conditions as mentioned above. Practically, β-cyclogeranyl phenyl sulfone alone can be obtained on a commercial scale by repeating the above mentioned operations. The recovered mixture from the mother liquor can be used untouched or after the removal of the higher boiling point impurities by molecular distillation.

Other features of the invention will become apparent in the course of the following descriptions of exemplary embodiments which are given for illustration of the invention and are not intended to be limiting thereof.

EXAMPLES

Example 1

(1) Synthesis of allylic chloride

Into the mixture of 188.5 g of myrcene (purity 83%, 1.15 mol), and 0.7 g of cuprous chloride (I), hydrogen chloride gas was bubbled until the disappearance of myrcene at 0° C.-8° C., and further agitated for 20 hours at that temperature. The reaction mixture was poured into 100 ml of water, extracted with 100 ml of toluene, and washed with 100 ml of water and 100 ml of a 5% sodium bicarbonate aqueous solution successively, after which the solvent was distilled off under reduced pressure, to get 235.3 g of oil. This oil was found to be a mixture of primary allylic chlorides (geranyl chloride and neryl chloride) and tertiary allylic chlorides (linalyl chloride) having a ratio of primary allylic chlorides to tertiary allylic chloride, 89.2 to 10.8, by gas chromatography.

Gas chromatography conditions:
column; PEG 20M, 2 m,
column temperature; 100° C. (after 2 minutes, the temperature was raised until 150° C. at a progressive rate of 10° C./minute).

(2) Synthesis of allylic sulfone

After the addition of 1000 ml of toluene to 215 g (1.07 mol) of sodium phenyl sulfinate dihydrate, water was distilled off using a water separator with heating of from 90° C. to 110° C. After cooling to 105° C., 3.76 g (10.2 mmol) of tetra-n-butylammonium iodide was added, after which 235.3 g of allylic chloride obtained by the above mentioned process was added dropwise over 20 minutes, and agitated for 2 hours at the same temperature. After cooling, solids were separated by filtration, after which the filtrate was washed with 100 ml of a 1% sodium thiosulfate aqueous solution, and 100 ml of water successively, and the solvent was distilled off to give 287.3 g of oil. This oil was found containing 261.2 g of the allylic sulfone. The yield from myrcene was 81%. The ratio of primary allylic sulfone to tertiary allylic sulfone was found 97.7 to 2.3.
  Gas chromatography conditions:
  column; Thermon 1000, 1 m,
    column temperature; 100° C. (the temperature was raised until 250° C. at a progressive rate 10° C./minute).
(3) Synthesis of cyclogeranyl phenyl sulfone In a three neck flask, 32.1 g of concentrated sulfuric acid (17.5 ml), 18.4 g of acetic acid (17.5 ml), and 50 ml of pentane were placed. To the mixture, 65.2 g (purity 90.9%, net 59.3 g) of allylic sulfone obtained by the above mentioned process, and 100 ml of pentane were added over 5 minutes. The inner temperature was increased to 38° C. After 5 minutes, the reaction mixture was poured into a mixture of ice and ethyl acetate (300 g and 300 ml). The flask was washed twice with cold water and the washes were added to the reaction mixture and extracted with 300 ml of ethyl acetate. The organic phase was washed with 500 ml of water, and 300 ml of 10% sodium bicarbonate aqueous solution successively, after which it was dried with magnesium sulfate. After the separation of magnesium sulfate, the solvent was distilled off to give 65.6 g (purity 81.3%, net 53.3 g) of yellowish brown viscous oil. The ratio of α-cyclogeranyl phenyl sulfone sulfone [1] to β-cyclogeranyl phenyl sulfone [2], [1]/[2] was found to be 23/77 by gas chromatography.
  Gas chromatography conditions:
  column; Thermon 1000, 1 m,
    column temperature; 150° C.–250° C., at a progressive rate of 16° C./minute.

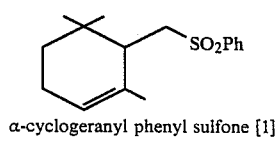

α-cyclogeranyl phenyl sulfone [1]

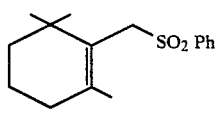

β-cyclogeranyl phenyl sulfone [2]

The oil obtained by the above mentioned process was dissolved in 100 ml of hexane at reflux, after which it was cooled gradually and kept 5 hours at 10° C., and 34.2 g of white crystal were separated by a glass filter. The crystals were found to be a mixture of [1] and [2], the ratio of [1]/[2] being 4/96 by gas chromatography. The solvent in the mother liquor was distilled off under reduced pressure to give 25.8 g of brown viscous oil (purity 74%, net 19.1 g). The obtained oil was found to be a mixture of [1] and [2], the ratio of [1]/[2] being 57/43.

Example 2–4, and Comparative Example 1

The reaction of phenyl sulfinates with the allylic chloride obtained by the method of Example 1 was conducted to obtain the corresponding allylic sulfone. The mole ratio of allylic chloride, phenyl sulfinate, and tetralkylammonium halide (catalyst), reaction conditions, and the kind of solvent were the same as the allylic sulfone synthesis according to Example 1. The results are shown in Table 1. The yield of (I)+(IV) was based on myrcene.

TABLE 1

|  | Phenyl sulfinate | Ratio of (I)/(IV)[1] | Catalyst[2] | Yield (%) |
|---|---|---|---|---|
| Example 2 | Potassium phenyl s.[3] | 97.0/3.0 | TBAI | 80.5 |
| Example 3 | Sodium p-tolyl s. | 97.0/3.0 | TBAI | 79.8 |
| Example 4 | Sodium phenyl s. | 97.7/2.3 | STAI | 80.8 |
| Comparative Example 1 | Sodium phenyl s. | 89.6/10.4 | TBAB | 75.0 |

Note;

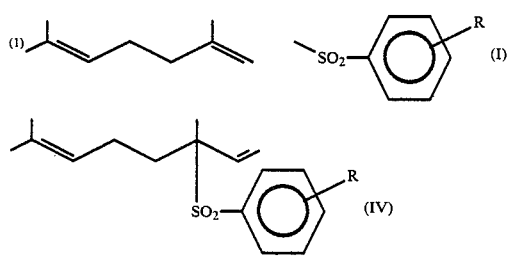

[2]TBAI: tetra-n-butylammonium iodide (n-Bu$_4$ NI)
TBAB: tetra-n-butylammonium bromide (n-Bu$_4$ NBr)
STAI: Stearyltrimethylammonium iodide (C$_{18}$H$_{37}$(CH$_3$)$_3$ NI)
[3]s. means sulfinate.

Comparative Example 2

The synthesis of geranyl phenyl sulfone was carried out according to the same process as Example 1 using allylic chloride obtained by the same method as Example 1 except omitting the water removal from sodium phenyl sulfinate dihydrate with toluene. The extract by the same method was found the mixture of primary sulfone (I) and tertiary allylic sulfone (IV), having the ratio of primary allylic sulfone to tertiary allylic sulfone 89.9/10.1, the yield of geranyl phenyl sulfone from myrcene was 53.8% by gas chromatography.

Example 5

In a three neck flask of capacity 200 ml, 10.0 g of concentrated sulfuric acid and 30 ml of hexane were placed and vigorously stirred. To this reaction mixture, 24.8 g of allylic sulfone (purity 80%, net 19.8 g) obtained by Example 3 and 30 ml of hexane were quickly added dropwise at inner temperature of 30°, and stirred vigorously for 5 minutes at 35° C.–40° C. inner temperature. 50 ml of ice water was poured into the reaction mixture and stirred for 5 minutes, after which the content was transferred into a separation funnel, and extracted with 200 ml of ethyl acetate. The organic phase was washed with 100 ml of a 5% sodium bicarbonate aqueous solution, and 100 ml of water 2 times successively, after which the solvent and lower boiling point part were distilled off by the use of an evaporator to give 21l.g (purity 83%, net 17.8 g) of brown viscous oil. The oil was found to be a mixture of [3] and [4], the ratio of [3]/[4] being 23/77 by gas chromatography.

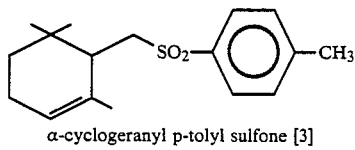

α-cyclogeranyl p-tolyl sulfone [3]

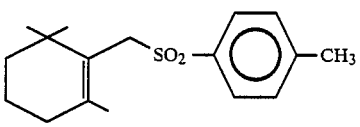

β-cyclogeranyl p-tolyl sulfone [4]

Gas chromatography conditions:
column, Thermon 1000, 1 m,
column temperature; 150° C.–250° C., at a progressive rate of 16° C./minute.

Example 6

(1) Synthesis of allylic chloride

In a three neck flask of one liter capacity, 50 g (0.325 mol) of linalool, and 26.9 g (0.341 mol) of pyridine were placed. To the mixture, 40.6 g (0.341 mol) of thionyl chloride was added in dropwise under vigorous stirring maintaining an inner temperature of 30° C., after which the content was stirred for 2.5 hours at the same temperature. The reaction mixture was poured into 500 ml of ice water, and the hexane layer separated. The hexane layer was washed with 100 ml of a 5% sodium bicarbonate aqueous solution, and 100 ml of a saturated sodium chloride aqueous solution successively, after which it was dried with magnesium sulfate. After drying, the magnesium sulfate was separated by filtration, the hexane was distilled off under reduced pressure to give 50.6 g of slightly yellowish oil. This oil was found in a mixture of tertiary allylic chloride (linalyl chloride) and primary allylic chlorides (geranyl chloride and neryl chloride), the ratio of tertiary allylic chloride to primary allylic chlorides being 31:69.

Gas chromatography condition:
column packing; PEG 20M, 2 m,
column temperature; 100° C., (after 2 minutes, the temperature was raised to 150° C. at a progressive rate of 10° C./minute).

(2) Synthesis of allylic sulfone

In a three neck flask of one liter capacity, 50.6 g of allylic chloride obtained by the above mentioned process, 53.2 of sodium phenyl sulfinate, 4.77 g of sodium iodide, 4.82 g zinc chloride, and 450 ml of dimethylformamide were placed, and stirred for 5 hours at an inner temperature of 60°–70° C. in an atmosphere of nitrogen. After the reaction, the solvent, dimethylformamide was distilled off, and the residue was poured into 500 ml of water. The separated oil was extracted with a total of 300 ml of ethyl acetate in 3 extractions. The extract of ethyl acetate solution was washed with 300 ml of water and 100 ml of a sodium chloride aqueous solution successively, after which it was dried with magnesium sulfate. After the separation of magnesium sulfate by filtration, the solvent was distilled off under reduced pressure to give 76.4 g of brown oil. The compound was found to contain 72.1 g of allylic sulfone. The total yield from linalool was 80% by liquid chromatography.

Liquid chromatography conditions:
column; μ-Porasil, 30 cm
eluent; ethyl acetate/hexane=1/9 flow rate; 2 ml/minute

Comparative Example 3

The synthesis of allylic sulfone was conducted by the same process according to Example 6 using allylic chloride synthesized by the same process according to Example 6 except the non-addition of zinc chloride and sodium iodide. After the same extraction process, the yield of allylic sulfone from linalool was 67% by liquid chromatography.

Example 7-9

To a three neck flask of one liter capacity, 50.6 g of allylic chloride obtained by the method of Example 6, 4.82 of zinc chloride, 450 ml of dimethylformamide, and the prescribed amount of sulfinate and iodide (shown in the following table) were placed and the reaction was conducted under the same condition of Example 6. The results are shown in the following table. The yield of the compound in the table is the total yield from linalool.

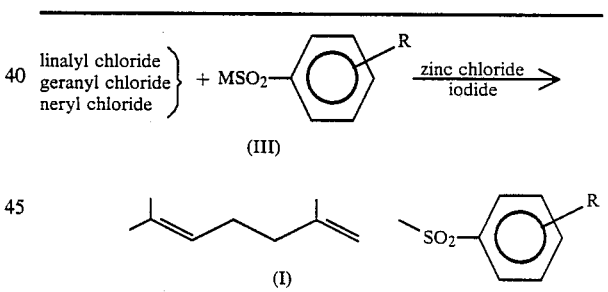

| Example No. | Kind of (III) | Amount (g) | Amount of iodide (g) | Yield of (I) (%) |
|---|---|---|---|---|
| 7 | Potassium phenyl sulfinate | 58.4 | NaI 4.77 | 78 |
| 8 | Potassium phenyl sulfinate | 58.4 | KI 5.28 | 80 |
| 9 | Sodium p-tolyl sulfinate | 57.7 | NaI 4.77 | 82 |

Example 10

By the distillation of 50.0 g of allylic chloride obtained by the process described in Example 6 with a distillation column of 30 cm length, packed with glass beads under reduced pressure, 8.2 g of distillate having the boiling point of 45° C.–50° C./0.3 mm Hg was obtained. The compound was found to be a mixture of tertiary allylic chloride (linalyl chloride) and primary allylic chlorides (geranyl chloride and neryl chloride), having the ratio of 95:5 by gas chromatography.

Gas chromatography condition:

column packing; PEG 20M, 2 m, column temperature; 100° C., (after 2 minutes, the temperature was raised to 150° C. at a progressive rate of 10° C./minute).

In a three neck flash of 200 ml capacity, 8.2 g of the mixture of tertiary allylic chloride and primary allylic chlorides, tertiary allylic chlorides being predominant over primary allylic chloride, 8.6 g of sodium phenyl sulfinate, 2.6 g of zinc chloride and 100 ml of dimethylformamide were placed, and stirred for 5 hours at an inner temperature of 60°–70° C. in an atmosphere of nitrogen. After the reaction, dimethylformamide was distilled off under reduced pressure, and the residual oil was poured into 200 ml of water. The separated oil was extracted with a total of 100 ml of ethyl acetate in 3 extractions. The ethyl acetate extract was washed with 200 ml of water and 100 ml of a saturated sodium chloride aqueous solution successively, after which it was dried with magnesium sulfate. After the separation of magnesium sulfate by filtration, the solvent was distilled off under reduced pressure to give 12.6 g of brown oil. The oil was found to contain 11.1 g of the allylic sulfone by liquid chromatography. The yield was 84%.

Liquid chromatography condition:
column; μ-Porasil, 30 cm,
eluent; ethyl acetate/hexane=1/9,
flow rate; 2 ml/minute

Example 11

The water from 64.53 g (0.32 mol) of sodium benzene sulfinate dihydrate was distilled off by a water separator with 300 ml of toluene heated from 90° C. to 110° C., after which it cooled to 105° C., 1.13 g (3.06 mmol) of tetra-n-butylammonium iodide was added, and further 50.6 g of allylic chloride obtained in Example 6 was added over 20 minutes dropwise, and stirred for 2 hours at the same temperature. After cooling, and separating the solid substances by filtration, the filtrate was washed with 30 ml of a sodium thiosulfate aqueous solution, and 30 ml of water, successively. The solvent was distilled off under reduced pressure to give 78.2 g of oil. In the product, 63.5 g of allylic sulfone was found by gas chromatography, and the yield from linalool was 70%. The ratio of primary allylic sulfone to tertiary allylic sulfone of the compound was 95.0 to 5.0.

Example 12

(1) Synthesis of allylic chloride

In a three neck flask of 100 ml capacity, 48.2 (purity 70.5%, 0.25 mol) of myrcene, 0.17 g of cuprous chloride, and 0.34 g of n-octyl sulfide were placed. Into this mixture, hydrogen chloride gas was bubbled. During the bubbling of hydrogen chloride gas, the inner temperature was controlled in the range of 10° C.–15° C. by cooling in an ice-bath and by the adjustment of the rate of bubbling. The hydrogen chloride gas bubbling was stopped when myrcene was not monitored by gas chromatography. The reaction mixture was poured into 100 ml of water after which 100 ml of hexane was added and the organic layer was separated. The organic layer was washed with 100 ml of a 2% sodium carbonate aqueous solution 2 times, and then with 100 ml of water. The solvent of the hexane solution was distilled off to give 101.4 g of brown oil. The ratio of tertiary allylic chloride (linalyl chloride) to primary allylic chlorides (geranyl chloride and neryl chloride) of the oil was 12:88 by gas chromatography. The yield of allylic chloride (the sum of linalyl chloride, geranyl chloride, and neryl chloride) was 87.4% with the internal standard of n-hexadecane by gas chromatography.

(2) Synthesis of allylic sulfone

The water of 45.9 g (0.23 mol) of sodium phenyl sulfinate dihydrate was removed by heating from 90° C. to 110° C. by a water separator with 300 ml of toluene. After cooling to 105° C., 0.8 g (2.2 mmol) of tetra-n-butylammonium iodide was added to the reaction mixture, and further 101.4 g of allylic chloride obtained by the above mentioned process was added dropwise over 5 minutes, after which it was stirred for 3 hours in refluxing toluene. After cooling and removing the solids by filtration, the filtrate was washed with 100 ml of a 1% sodium thiosulfate aqueous solution, and 100 ml of water successively, after which the solvent was distilled off under reduced pressure to give 62.0 g of oil. The allylic sulfone was 54.7 g by gas chromatography and the yield from myrcene was 78.7%. The ratio of primary allylic sulfone to tertiary allylic sulfone was 98 to 2.

Example 13 and 14

Example 12 was repeated except that instead of 0.34 g of n-octyl sulfide, there were used organic sulfides in the amounts indicated in Table 2. The results are shown in Table 2.

TABLE 2

| Example No. | Organic sulfide | Amount (g) | Ratio of tertiary allylic chloride: primary allylic chloride | Yield of allylic chloride (%) |
| --- | --- | --- | --- | --- |
| 13 | n-hexyl sulfide | 0.34 | 12:88 | 85.6 |
| 14 | phenyl sulfide | 0.34 | 15:85 | 84.2 |

Comparative Example 4

Example 12 was repeated except with no n-octyl sulfide. The ratio of tertiary allylic chloride to primary allylic chloride in the product was 30:70, and the yield of total allylic chloride was 85.2%.

Comparative Example 5

Example 12 was repeated except with no n-octyl sulfide until the end of hydrogen chloride gas bubbling. The ratio of tertiary allylic chloride to primary allylic chloride to this point was 32:68. After the obtained reaction mixture had been stirred for 15 hours at 10° C., Example 12 was repeated as to work-up procedure and analysis. The ratio of tertiary allylic chloride to primary allylic chloride was 13:87, and the yield of total allylic chloride was 83.4%.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for preparing an allylic sulfone of the following formula (I),

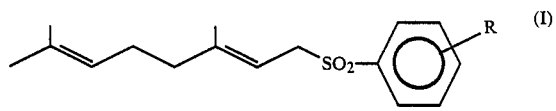

wherein, R is a hydrogen atom, or a lower alkyl group, and containing both cis and trans isomers, which comprises reacting a compound selected from the group consisting of geranyl chloride, neryl chloride, and linalyl chloride, with a phenyl sulfinate of the following formula (III),

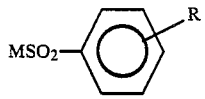

wherein, R is a hydrogen atom, or a lower alkyl group, and M is a sodium atom or potassium atom, in the presence of (i) tetralkylammonium iodide in an anhydrous condition, or (ii) a zinc halide and an iodide compound.

2. The process according to claim 1, wherein the reaction in the presence of (i) tetralkylammonium iodide is carried out in an aliphatic or aromatic hydrocarbon solvent.

3. The process according to claim 1, wherein the reaction is carried out at a temperature in the range of from 0° C. to 150° C.

4. A process for preparing an allylic sulfone of the following formula (I),

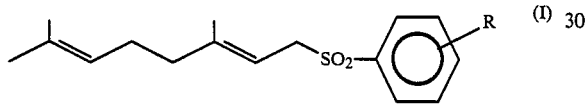

wherein, R is a hydrogen atom or a lower alkyl group, and containing both cis and trans isomers, which comprises the steps of:
(1) reacting myrcene with hydrogen chloride, or reacting linalool with thionyl chloride; and
(2) reacting a mixture of geranyl chloride, neryl chloride and linalyl chloride obtained in step (1), with a phenyl sulfinate of the following formula (III),

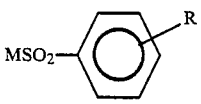

wherein, R is a hydrogen atom or a lower alkyl group, and M is sodium atom or potassium atom, in the presence of (i) tetralkylammonium iodide in an anhydrous condition, or (ii) a zinc halide and an iodide compound.

5. The process according to claim 4, wherein the reaction of a mixture of chlorides with a phenyl sulfinate in the presence of tetralkylammonium iodide is carried out in an aliphatic or aromatic hydrocarbon solvent.

6. The process according to claim 4, wherein the reaction of a mixture of said chlorides with a phenyl sulfinate is carried out at a temperature in the range of from 0° C. to 150° C.

7. The process according to claim 4, wherein the reaction of myrcene with hydrogen chloride is carried out in the presence of a copper catalyst.

8. The process according to claim 7, wherein the reaction is carried out in the presence of an organic sulfide.

9. The process according to claim 4, wherein the reaction of linalool with thionyl chloride is carried out in the presence of an amine.

10. A process preparing for a cyclogeranyl sulfone of the following formula (II)

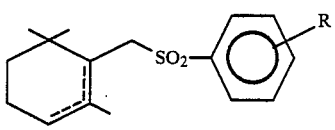

wherein, R is a hydrogen atom or a lower alkyl group, and a double bond exists at either one of the dotted positions, which comprises the steps of:
(1) reacting a compound selected from the group consisting of geranyl chloride, neryl chloride, and linalyl chloride, with a phenyl sulfinate of the following formula (III),

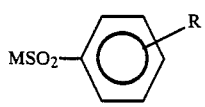

wherein, R is a hydrogen atom or a lower alkyl group, and M is sodium atom or potassium atom, in the presence of (i) tetralkylammonium iodide in an anhydrous condition, or (ii) a zinc halide and an iodide compound; and
(2) cyclizing an allylic sulfone of the following formula (I),

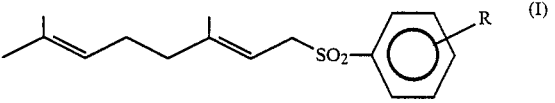

wherein, R is a hydrogen atom or a lower alkyl group, and containing both cis and trans isomers obtained in step (1) in the presence of an acid catalyst.

11. The process according to claim 10, wherein the reaction in the presence of (i) tetralkylammonium iodide is carried out in an aliphatic or aromatic hydrocarbon solvent.

12. The process according to claim 10, wherein the reaction of a compound selected from the group consisting of geranyl chloride, neryl chloride, and linalyl chloride, with a phenyl sulfinate is carried out at a temperature in the range of from 0° C. to 150° C.

* * * * *